United States Patent
Green et al.

(10) Patent No.: US 6,888,467 B2
(45) Date of Patent: *May 3, 2005

(54) GAS DETECTION INSTRUMENT AND METHOD FOR ITS OPERATION

(75) Inventors: David C. Green, Canonsburg, PA (US); Wenfeng Peng, Mississauga (CA); Chuan-Bao Wang, Oakdale, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 148 days.

This patent is subject to a terminal disclaimer.

(21) Appl. No.: 10/314,965

(22) Filed: Dec. 10, 2002

(65) Prior Publication Data

US 2004/0113802 A1 Jun. 17, 2004

(51) Int. Cl.[7] ............................................. G08B 17/10
(52) U.S. Cl. ...................... 340/632; 340/628; 340/629; 340/630; 340/633; 340/634; 73/23.31; 73/23.2; 73/31.05; 73/31.07
(58) Field of Search ................................ 340/632, 628, 340/629, 630, 633, 634, 693.5, 584; 73/23.31, 23.2, 31.05, 31.07, 49; 436/143, 156; 422/98, 159; 364/550, 496, 509, 510

(56) References Cited

U.S. PATENT DOCUMENTS

| | | | | |
|---|---|---|---|---|
| 5,234,837 A | * | 8/1993 | Accorsi et al. | 436/159 |
| 5,780,715 A | * | 7/1998 | Imblum | 73/23.21 |
| 5,879,631 A | * | 3/1999 | Wewers et al. | 422/98 |

* cited by examiner

Primary Examiner—Hung Nguyen
(74) Attorney, Agent, or Firm—Dennison, Schultz, Dougherty & MacDonald

(57) ABSTRACT

A gas detection instrument comprises a combustible gas sensor and associated circuitry, which supplies power to the sensor and measures and displays resulting sensor response. The supplied power is switched between timed pulses of electricity and steady state electricity, with the intermittent electricity being employed only when no significant change in sensor output has been detected. Alternatively, timed pulses of electricity are maintained, and predictive software algorithms are used to give readings for gas concentration during interruption of the power supply. The sensor operation enables the instrument to respond to rapid changes in gas concentration while minimizing power consumption of the sensor.

16 Claims, 3 Drawing Sheets

GAS DETECTION INSTRUMENT AND METHOD FOR ITS OPERATION

BACKGROUND OF THE INVENTION

1. Field of the Invention

The invention relates to a gas detection instrument having a combustible gas sensor, which requires power to heat one or two sensor elements in order to generate a signal corresponding to gas concentration.

2. Description of Related Art

Combustible gases present a significant hazard in the work place. At the present time, there are mainly three sensor technologies available for detecting combustible gases, the pellistor or catalytic bead sensor, the metal oxide semiconductor sensor, and the infrared sensor. Among the three technologies, the catalytic bead and semiconductor sensors are most widely used in the safety market due to their low costs and compact sizes.

Catalytic bead sensors started out as hot-wire gas detectors, in which the change in resistance of a heated platinum filament due to combustion of the gas on the surface of the wire provided the detection signal. Greatly improved performance, especially with respect to poisoning, was achieved by forming a porous bead of alumina (or other refractory material) around the coil, and then applying a precious metal catalyst to the surface, and within the bulk of the alumina bead. This catalytic bead sensor operates by heating the bead to about 500–600° C. by internal electrical heating, and then measuring small changes in the electrical resistance of the bead in the presence of a combustible gas due to the increase in temperature caused by gas combustion.

This small resistance change is typically measured using a Wheatstone bridge circuit. The majority of catalytic bead sensors have two beads, a catalytic bead and a reference bead which is not catalytically active but which is used to compensate for changes in the electrical resistance of the catalytic bead due to changes in ambient conditions.

Metal oxide semiconductor (MOS) sensors are long-lived, and more sensitive to combustible gases. A MOS sensor typically comprises a sintered metal (tin, zinc, or iron) oxide film on an alumina or silica substrate, which surrounds a heater coil. Two noble metal electrodes are applied to the oxide-coated substrate. This entire sensing element is enclosed in a metal housing with a stainless steel mesh cover acting as both a flame arrestor and a gas entry port. During operation, the sensing element is heated to about 250–350° C. When gas enters the sensor, it interacts with the oxide coating, causing a decrease in resistance between the two electrodes. The output of the MOS sensor varies logarithmically with the gas concentration. The accuracy, repeatability, and stability of MOS sensors are poor compared with catalytic bead sensors.

Combustible gas sensors require power to operate. As has been noted, the sensing elements in these sensors must be heated to a certain temperature in order to detect gas, and the sensors thus have a power consumption which is typically above 200 mW. This power requirement has been a major concern when designing a portable gas detection instrument, where available battery power determines the run time of the instrument.

In order to reduce power consumption, electricity may be supplied to the sensor at given intervals, as proposed in Japanese Provisional Utility Model Publication No. 14959 of 1987. This intermittent operation saves about 30–60% power, while at the same time, allows gas detection. This sensor operation, however, has a major drawback. The duration of electricity supply in each interval must be sufficiently long for the sensing element of the sensor to be heated up to desired temperature to detect gas; otherwise sensor sensitivity and accuracy will be affected. The intervals of power supply are, therefore, generally limited to at least a few seconds, which means a long waiting period for the instrument to detect, and update visual display and activate an audible alarm in the presence of gas.

U.S. Pat. No. 6,348,872 discloses a gas detector which comprises a hot-wire sensor and an actuating power control that supplies pulsed actuating power with two pulse cycles. When the gas concentration detected by the sensor is low a long cycle is used; when the gas concentration exceeds a prescribed level a shorter pulse cycle is used. This instrument has about the same limitations as other instruments with intermittent power supply due to the minimum requirement for duration of each cycle.

Japanese Provisional Patent Publication 03-233699 describes a combustible gas detector in which the sensor is operated with intermittent power, but the power is changed to continuous power in the presence of gas. The instrument continues to supply power as long as gas is present. Although the instrument is capable of detecting transient changes in gas concentration and is especially good for monitoring the occurrence of gas leakage, continued heating of sensing elements substantially increases power consumption in the presence of gas.

SUMMARY OF THE INVENTION

It is therefore an object of the invention to provide a method for operating an instrument for the detection of combustible gases that reduces power consumption.

It is a further object of the invention to provide an instrument capable of detecting transient changes in gas concentration, and of triggering an alarm within the shortest possible time after the gas concentration exceeds a preset level.

To achieve these and other objects, the invention is directed to a gas detection instrument and method for its operation, including circuitry which supplies power to the sensor in a manner which reduces power consumption.

In a first embodiment of the invention, the supplied power is switched between intermittent electricity flow and steady state electricity flow with the intermittent current flow being employed only when no significant change in sensor output is detected. This mode of sensor operation enables the instrument to respond to rapid changes in gas concentration while minimizing power consumption of the sensor throughout use.

In another embodiment of the invention, the sensor is constantly operated with intermittent electricity flow. The instrument uses predictive software algorithms to extrapolate readings for gas concentration during interruption of power based on sensor response immediately before power interruption.

DESCRIPTION OF THE PREFERRED EMBODIMENTS

Figure 1:
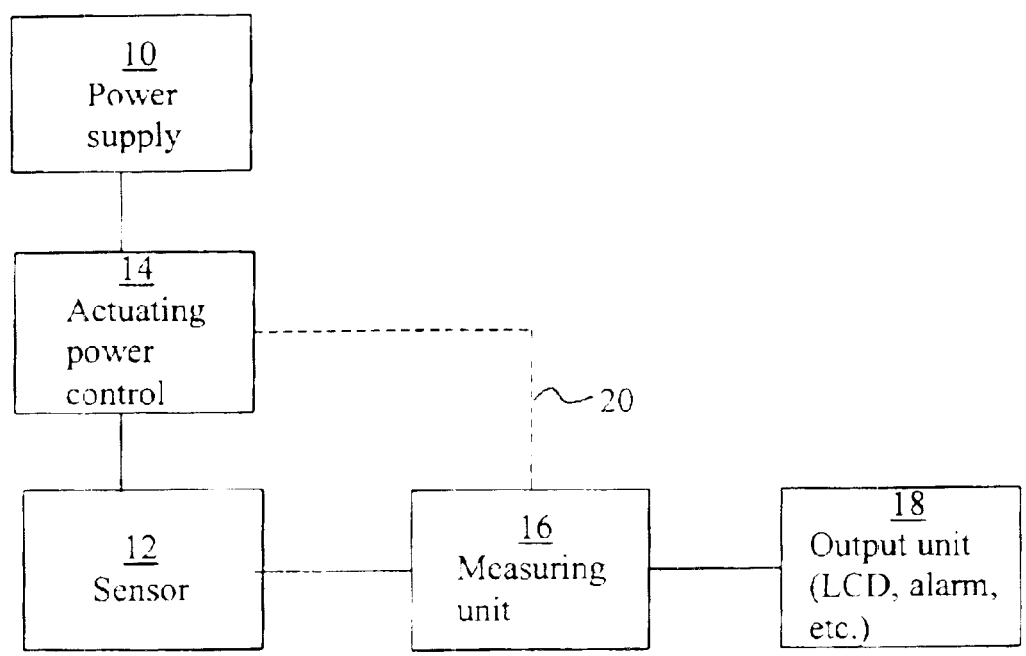
FIG. 1 is a schematic diagram of an embodiment of a gas detection instrument according to the invention.

FIG. 1 illustrates an embodiment of a gas detection instrument according to the invention. The instrument includes five major parts, a power supply 10, a sensor 12, an actuating power control unit 14 that operates the sensor, a unit 16 for measuring sensor output, and an output unit 18, which may include an LCD display, an audible alarm, or other audio and/or visual output. The sensor 12 is a combustible gas sensor, and it may be a catalytic bead sensor or a semiconductor (MOS) sensor, as discussed above. The power supply 10, which is usually a battery pack, provides electricity for operation of the entire unit. The power supplied to the sensor 12 is controlled by the actuating power control unit 14. For either the semiconductor sensor type or the catalytic bead type, the energy to the sensor, and especially to the sensing elements, may be in the form of a constant voltage, constant current, or constant power. The voltage, current, or power is selected to be adequate to heat the sensor to a desired and predetermined operating temperature. The measuring unit 16 includes circuitry which detects changes in an electrical parameter, for example the electrical resistance, of the sensing elements in the sensor, and converts the change to an output signal. Typically the measuring unit includes a Wheatstone bridge circuit when the sensor is of the catalytic bead type. There is a feedback link 20, as shown by the dashed lines in FIG. 1, between the measuring unit and the actuating control unit, so that the power supplied to the sensor can be adjusted according to changes in sensor output signal detected by the measuring circuit. The measured results are presented by the output unit 18, which can be an LCD, an alarm, or another device or a combination of other devices as known to those of ordinary skill in the art. When digital devices are included, the output unit should include an A/D converter and possibly a microprocessor for processing the signal from the sensor and managing output devices.

Figure 2:
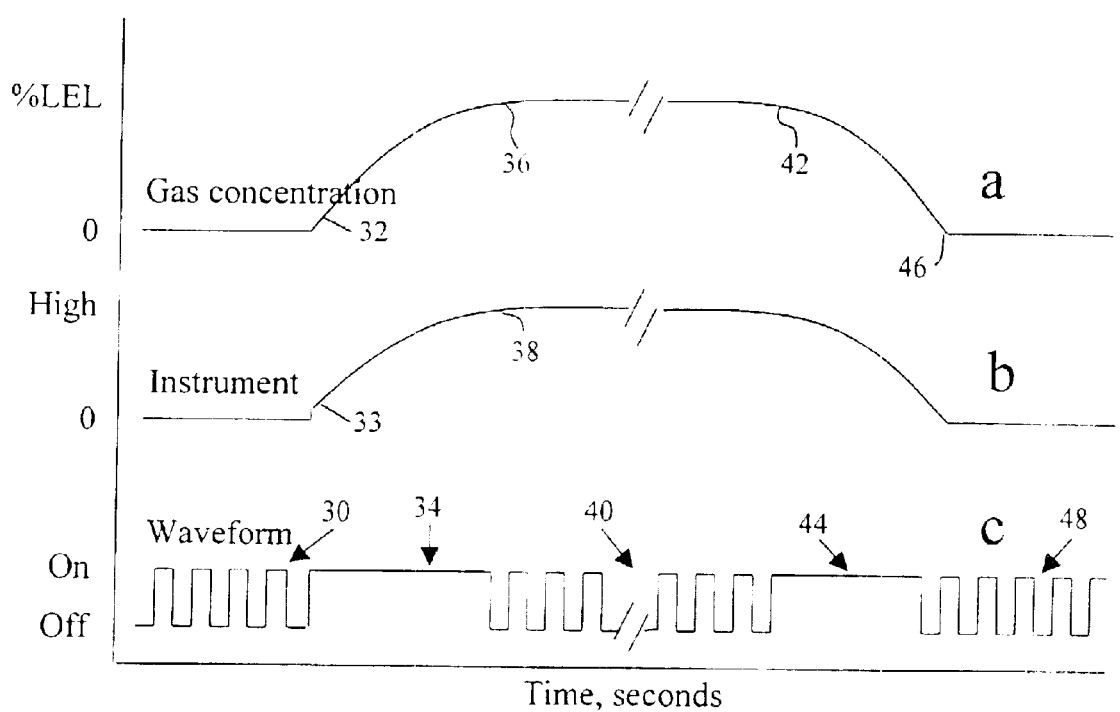
FIG. 2 is a graph showing sensor operation vs. time for an embodiment of the invention.

FIG. 2 illustrates the working principle of the embodiment of FIG. 1, showing gas concentration (curve a) as a percentage of lower explosive limit (% LEL), instrument response (curve b) from 0 to high, and electricity supply (curve c) as off or on. In the absence of a combustible gas (concentration 0), the actuating control unit supplies electricity intermittently to the sensor (time period 30). In this case the power is in the form of a plurality of substantially identical pulses of voltage. Since it typically takes ~2 seconds to heat a commercial catalytic bead sensor, or ~1 second to heat a semiconductor sensor to the operating temperature (~250–500° C.), the duration of power supply is typically one or more seconds and the duration of rest in one cycle depends on how much power is projected to be saved. When a significant change in gas concentration (point 32) causes a corresponding change in the sensor's output (point 33), it is detected by the measuring unit. When the change in sensor output exceeds a predetermined value, the actuating control unit instantly changes to steady state electricity (time period 34), during which the sensor output keeps changing and the instrument measures output of the sensor at a more frequent basis. Accordingly, instrument output devices such as LCD display and alarm, can be updated at the same frequency. In practice, it is preferred to have a portable gas detection instrument update the measured reading once a second.

When no further significant change in gas concentration occurs (point 36), the sensor output reaches a stable reading (point 38), and the actuating control unit changes back to the pulsed power mode (time period 40).

The same mechanism applies when the gas concentration starts decreasing (point 42). The actuating control unit switches to steady state power (time period 44) and the instrument updates its output more often in order for instrument output devices to follow the rapid changes in gas concentration. Once the gas concentration returns to zero (point 46), the measuring circuit detects no further significant change in sensor output and this information is fed back to the actuating control unit, after which the operating power returns to intermittent or pulsed mode (time period 48).

The pulsed electricity is typically represented by the square waveform shown in FIG. 2, but many other waveforms are possible in the spirit of the invention. The threshold value for switching between intermittent current and steady state current is selected based on the signal-to-noise ratio of the output signal, the effects of ambient conditions such as temperature and humidity on the output signal, and the alarm settings of the instrument. For example, a typical commercial catalytic bead sensor possesses a transient response in the range of ±3% LEL when there is a sudden, large change in temperature and/or humidity. The instrument alarm may be set at a level as low as 10% LEL. The threshold value for switching power applied to the sensor is preferable 3–5% LEL, which is higher than sensor's response to changes in ambient conditions, and significantly lower than the alarm setting to allow steady state operation when sensor output signal rises in order to take full advantage of the invention.

Figure 3:
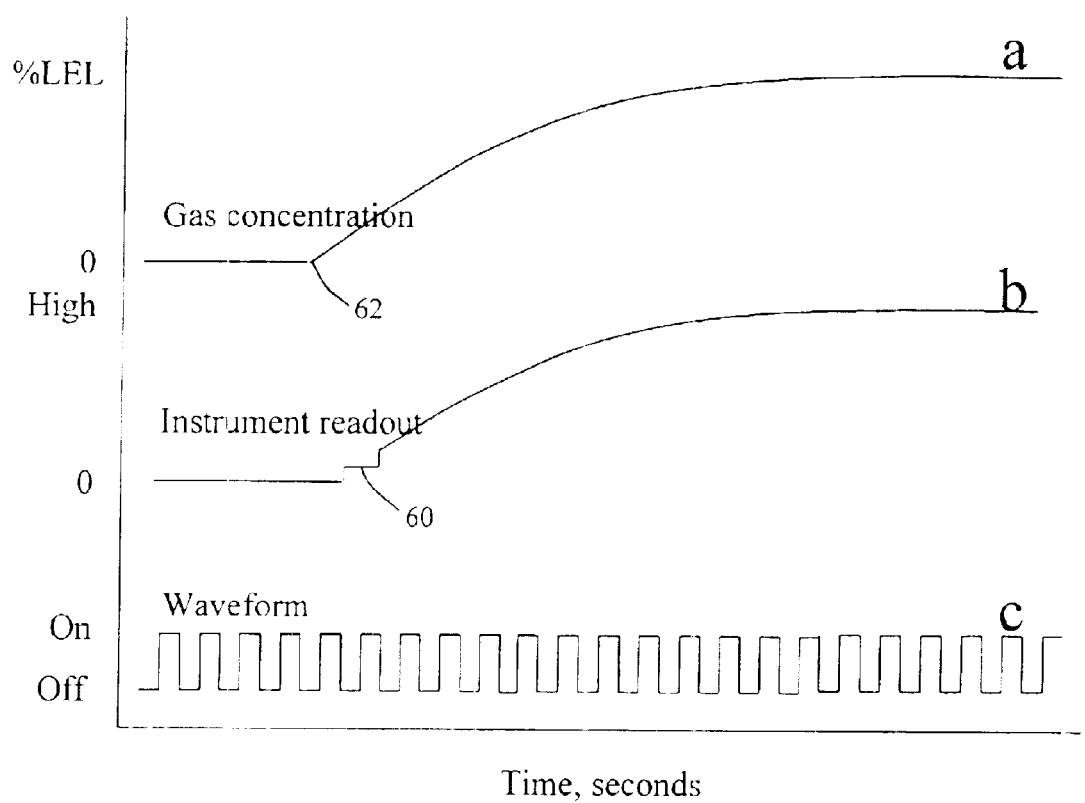
FIG. 3 is a graph showing sensor operation vs. time for another embodiment of the invention.

In another embodiment of the invention shown in FIG. 3, pulsed power is combined with trend analysis or extrapolation techniques to provide updated instrument outputs with an interval less than or equal to one second. In this embodiment, the feedback link 20 between the actuating power control unit and the sensor measuring unit is omitted. Pulses of electricity are applied to the sensor on a continuous basis, even when the presence of a combustible gas has been detected. In practice, the total cycle time for a power pulse is typically between 3–8 seconds; shorter times are difficult to achieve because of the minimum time required to heat the sensing elements of the sensor for reliable gas detection. This means that the time for updating the output is about 3–8 seconds even when the gas concentration changes quickly with time. In order to compensate for the less frequent updating, extrapolation is used to obtain new instrument output data at intervals of about 1 second. As shown in curve b of FIG. 3, the instrument starts to update its output (point 60) after continuous changes in the gas concentration (point 62) have been detected by the measuring circuit. An accurate read-out of the change in concentration usually requires at least 2 consecutive cycles after the occurrence of the change. The microprocessor in the instrument calculates the rate of change in sensor output, and predicts sensor outputs or instrument readouts for the next few seconds based on existing data and the rate of change calculated. An extrapolation method or other algorithm can be employed.

The calculation method can be written into software and stored in the microprocessor. The predicted data are sent to the output unit, and are used for updating the instrument readout until an actual sensor output signal is obtained in the next power cycle. It is understood that the more actual sensor output data are obtained, the closer the predictive data are to actual gas concentration.

What is claimed is:

1. A method for operating an instrument for detecting a combustible gas comprising a sensor including a heated surface on which the combustible gas reacts to cause a change in an electrical parameter output of the sensor, an electrical power supply for the instrument including a connection for heating the heated surface, a measuring unit for measuring gas concentration based on the output from the sensor, and an output display indicating a presence of combustible gas, comprising the steps of:

providing an actuating means for actuating the power supply;

providing a feedback link between the measuring unit and the actuating means;

supplying timed pulses of electricity from the power supply to the sensor, the pulses being of sufficient duration to enable the gas to react; and determining, with the measuring unit, the sensor output resulting from the reaction of the gas; and further supplying power to the sensor such that:

when the change in said sensor output is less than a predetermined threshold value, continuing supplying said timed pulses of power to the sensor, and when the change in said sensor output is at least equal to said threshold value, supplying continuous power to the sensor to enable continuous measurement of said sensor output.

2. The method of claim 1, wherein the sensor is a semiconductor sensor comprising a heater element and a metal oxide doped with catalyst which is heated by the heater element.

3. The method of claim 2, wherein the metal oxide is selected from the group consisting of oxides of tin, zinc, iron, and mixtures thereof.

4. The method of claim 1, wherein the sensor is a hot-wire sensor, the hot wire comprising a platinum filament.

5. The method of claim 1, wherein the sensor is a catalytic bead sensor with at least one bead comprising a catalyst doped ceramic formed on a fine platinum coil.

6. The method of claim 1, wherein the pulses are substantially identical pulses.

7. A method for operating an instrument for detecting a combustible gas comprising a sensor including a heated surface on which the combustible gas reacts to cause a change in an electrical parameter output, an electrical power supply for the instrument including a connection for heating the heated surface, a measuring unit for measuring gas concentration based on said sensor output, and an output display indicating a presence of combustible gas, comprising the steps of;

supplying timed pulses of electricity from the power supply to the sensor, the pulses being of sufficient duration to enable the gas to react; and calculating by algorithm, with the measuring unit, gas concentration for periods of time during which the sensor does not receive the pulses of power.

8. The method of claim 7, wherein software containing the algorithm is contained in the measuring unit.

9. The method of claim 7, wherein the algorithm extrapolates a value for gas concentration.

10. The method of claim 7, wherein the sensor is a semiconductor sensor comprising a heater element and a metal oxide doped with catalyst which is heated by the heater element.

11. The method of claim 10, wherein the metal oxide is selected from the group consisting of oxides of tin, zinc, iron, and mixtures thereof.

12. The method of claim 7, wherein the sensor is a hot-wire sensor, the hot wire comprising a platinum filament.

13. The method of claim 7, wherein the sensor is a catalytic bead sensor with at least one bead comprising a catalyst doped ceramic formed on a fine platinum coil.

14. The method of claim 7, wherein the pulses are substantially identical pulses.

15. An apparatus for detection of combustible gases, comprising;

a combustible gas sensor comprising heating means heated by electrical energy which enables reaction of the combustible gas, and an electrical parameter output which changes with concentration of combustible gas;

an electrical power supply including means for heating the heating means;

a measuring unit for determining concentration of combustible gas based on sensor output;

an output unit for displaying gas concentration determined by the measuring unit; and an actuating unit for the power supply including a feedback link for receiving data from the measuring unit, said actuating unit including means for instructing the power supply to supply timed pulses of electrical energy to the sensor when the sensor output changes by less than a predetermined threshold value, and for instructing the power supply to supply electrical energy continuously to the sensor when the sensor output changes by an amount at least equal to a predetermined threshold value.

16. An apparatus for detection of combustible gases, comprising;

a combustible gas sensor comprising heating means heated by electrical energy which enables reaction of the combustible gas, and an electrical parameter output which changes with concentration of combustible gas;

an electrical power supply including means for heating the heating means;

a measuring unit for determining concentration of combustible gas based on sensor output;

an output unit for displaying gas concentration determined by the measuring unit; and an actuating unit for supplying timed pulses of electrical energy to the sensor, wherein the measuring unit comprises software for extrapolating present gas concentration from at least one previous determination of sensor output.

\* \* \* \* \*